United States Patent [19]

Zappala

[11] 4,223,407

[45] Sep. 23, 1980

[54] HAIRDRESSING PROTECTIVE VISOR

[76] Inventor: Mary C. Zappala, 4816 Redwood Dr., Garland, Tex. 75043

[21] Appl. No.: 948,435

[22] Filed: Oct. 4, 1978

[51] Int. Cl.² .......................... A61F 9/00; A42D 1/12
[52] U.S. Cl. ........................................................ 2/174
[58] Field of Search ................. 2/174, 209, 12; 4/159

[56] References Cited

U.S. PATENT DOCUMENTS

| | | | |
|---|---|---|---|
| 1,750,937 | 3/1930 | Morgan | 2/174 X |
| 2,696,008 | 12/1954 | Penman et al. | 2/174 |
| 2,729,823 | 1/1956 | Foster | 2/174 |
| 2,763,869 | 9/1956 | Bogart et al. | 2/174 |
| 3,530,509 | 9/1970 | Simpson et al. | 2/209 |

FOREIGN PATENT DOCUMENTS 6944 of 1915 United Kingdom ........................ 2/174
1017305 1/1966 United Kingdom ........................ 2/174

*Primary Examiner*—Peter P. Nerbun
*Attorney, Agent, or Firm*—Hubbard, Thurman, Turner, Tucker & Glaser

[57] ABSTRACT

A visor for protecting a user's face from exposure to hairdressing preparations, such as shampoo, during hairdressing operations. The visor includes a fluid-tight extending across the person's forehead from one ear to the other, a trough attached to the fluid sealing means, and a brim extending out over the user's face from the trough. A pair of ear pieces are attached to the ends of the trough for holding the visor to the user's forehead. In a preferred form, the earpieces include full ear covers which extend the fluid-tight seal along the top and back of the user's ears and extend over the user's ears to completely protect the ears.

5 Claims, 8 Drawing Figures

U.S. Patent Sep. 23, 1980 4,223,407
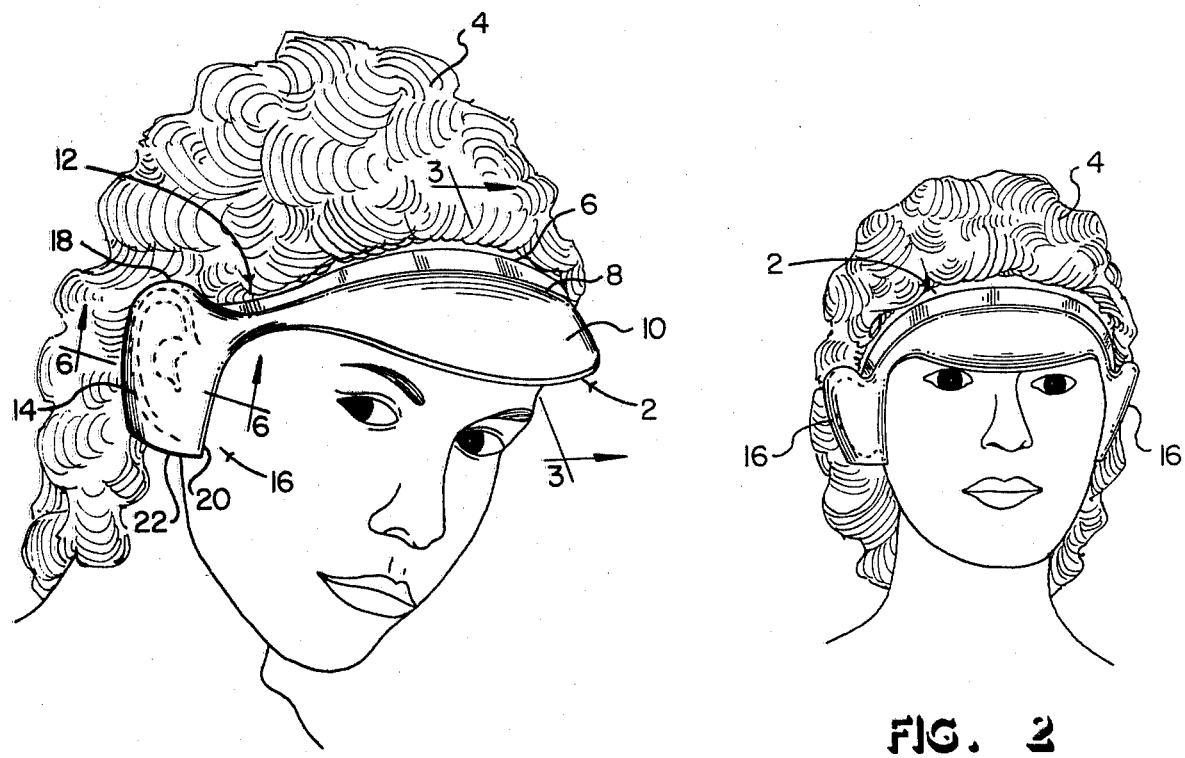
FIG. 1
FIG. 2
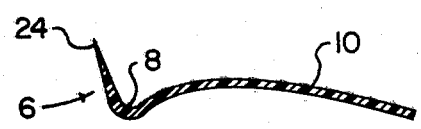
FIG. 3
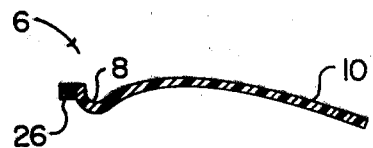
FIG. 4
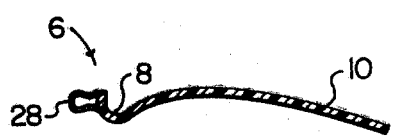
FIG. 5
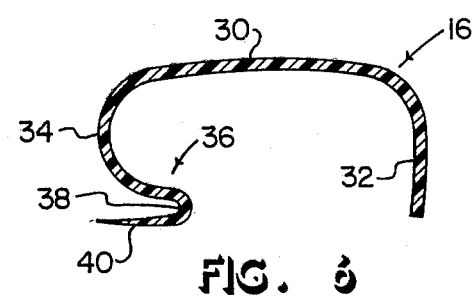
FIG. 6
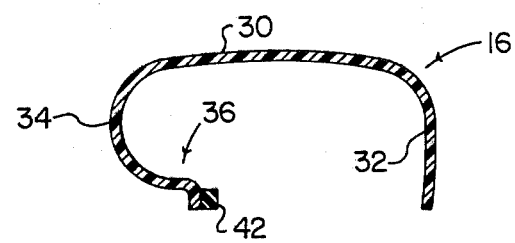
FIG. 7
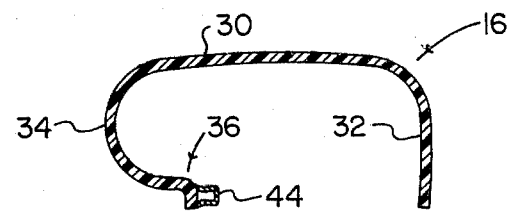
FIG. 8

HAIRDRESSING PROTECTIVE VISOR

BACKGROUND OF THE INVENTION

This invention relates to protective visors and more particularly to a visor for protecting a user's face from hairdressing preparations applied to the user's hair.

It is well-known that many hairdressing preparations should not be allowed to contact the face, ears, and, particularly, the eyes of the user. For example, most shampoos cause severe pain if allowed to get into the user's eyes. In addition, many other hairdressing preparations, including permanents and haircoloring, can cause actual damage to the eyes, ears, and face of the user. It is therefore desirable to have some means for preventing the flow of hairdressing preparations into the user's eyes, and preferably for directing the flow away from the user's eyes, ears, and face entirely.

SUMMARY OF THE INVENTION

Accordingly, an object of the present invention is to provide a visor for protecting the user's eyes, ears, and face from hairdressing preparations applied to the user's hair.

According to the present invention, a protective visor includes a fluid sealing band extending across the user's forehead substantially from one ear to the other, a trough, also extending from one ear to the other, having one edge connected to the fluid sealing band, a brim connected to the second edge of the trough extending out over the user's face, and earpieces connected to the ends of the trough and sealing band for holding the visor to the user's forehead. In a preferred form, the earpieces include cup-shaped ear covers, including an extension of the sealing band over the top and down the back of the user's ear.

BRIEF DESCRIPTION OF THE DRAWINGS

The present invention may be better understood by reading the following detailed description of the preferred embodiment with reference to the drawings wherein;

FIG. 1 is a side view of a protective visor in place on a user's head;

FIG. 2 is a front view of the protective visor of FIG. 1;

FIGS. 3, 4, and 5 are cross-sectional views of the forehead portion of various embodiments of the visor of FIG. 1, and FIGS. 6, 7, and 8 are cross-sectional views of various embodiments of the earpiece portion of the visor of FIG. 1.

DESCRIPTION OF THE PREFERRED EMBODIMENTS

FIGS. 1 and 2 illustrate side and front views of a visor shown generally at 2 in place on the forehead of a user 4. The visor 2 consists generally of a fluid sealing band 6 in contact with the user's forehead, a fluid trough 8 adjacent to band 6 and a brim portion 10 extending from the trough 8. The fluid seal band 6 and trough 8 extend substantially all the way across the user's forehead to a point 12 near the user's ear 14. The brim 10 is widest at the center of the user's forehead and tapers down until it is merely a narrow extension of trough 8 at the point 12.

The visor 2 is held in position by earpieces 16 which may be simple hook-type earpieces commonly used on eyeglasses. In the preferred embodiment illustrated in the FIGS. 1 and 2, the earpieces 16 are generally cup-shaped members providing protection from the hairdressing preparation for the ears. This earpiece 16 includes an extension of the fluid sealing band 6 along its edge 18 from point 12 across the top of the ear and down the back of the ear. The earpiece 16 covers the ear and has an edge 20 in close proximity to or touching the user's face in front of the ear. A lower edge 22 of earpiece 16 is open to allow circulation to the ear 14.

In use, the visor 2 is worn on the user's head as illustrated in FIGS. 1 and 2. When hairdressing preparations, such as shampoo, are applied to the hair, they tend to run down the scalp of the user 4 and across the forehead towards the eyes and face. Fluid sealing band 6 stops the flow of this liquid whereupon it is collected in trough 8. The trough 8 directs the fluid to the sides of the user's face instead of allowing it to run down the brim and drip off onto the user's face. The fluid will flow to point 12 whereupon it will typically flow across the earpiece 16 and drip off the bottom of it. Preferably, the trough 8 is extended beyond point 12 and across the top of earpiece 16 so that all the run-off fluid flows behind ear 14.

FIGS. 3, 4, and 5 illustrate cross-sections of the center of various embodiments of the visor 2. In each of these embodiments the trough 8 and brim 10 are essentially the same. These portions of the visor are preferably made from a relatively soft, flexible, but resilient plastic material which can be easily molded. Polyethylene is a preferable material which is also highly resistant to various hairdressing preparations, such as permanents.

In FIG. 3, the fluid sealing band 6 is a tapered edge 24 formed on one side of trough 8. With a material such as polyethylene, this edge 24 can be tapered down to a very thin and, therefore, very flexible border. In this way, when the visor is pressed against the user's forehead, the edge 24 will conform to the exact shape of the user's forehead and form a fluid-tight seal. As illustrated in FIG. 3, the edge 6 should be slanted toward the user's forehead at an acute angle of less than about 45°.

An alternate sealing band 6 is illustrated in FIG. 4 in the form of a band of a porous spongy material 26 bonded to one side of trough 8. The band 26 is preferably made from a closed cell foamed plastic so that it is impermeable to the hairdressing liquids. But if desired, band 26 may be similar to the fluid absorbing sweatbands commonly used.

A third form of fluid sealing band 6 is illustrated in FIG. 5 as a generally tubular envelope 28 attached to the one edge of trough 8. This envelope 28 is preferably made from a very flexible sheet of impermeable material which may also be polyethylene or a vinyl material which may be bonded to the material forming trough 8 and brim 10. The envelope 28 is preferably fluid-filled and the use of a gas is preferred because of its light weight, but a liquid would otherwise be quite suitable. Such fluid-filled envelopes are quite effective at forming a fluid-tight seal against irregular surfaces and thus may be preferred over the fluid seals illustrated in FIGS. 3 and 4. The embodiment illustrated in FIG. 5 has the disadvantage of comprising a number of separate pieces which must be assembled to provide the final complete visor.

FIGS. 6, 7, and 8 are cross-sectional illustrations of various forms of the earpiece 16 according to the present invention. Each of these illustrations is basically a view from the bottom of earpiece 16, that is, looking at the bottom edge 22. Each of these earpieces has essentially the same cup-shaped form in which the bottom 30 of the cup-shape protects the majority of the ear while one side 32 extends to the face in front of the ear and a second side 34 extends behind and to the back side of the ear to a fluid sealing and ear engaging portion shown generally at 36.

The FIG. 6 embodiment corresponds to the FIG. 3 embodiment and has a trough 38 which is preferably an extension of the trough 8 of FIG. 3. As in FIG. 3, one side of trough 38 tapers to a very thin edge 40 to form a fluid-tight seal against the user's scalp behind the ear. This FIG. 6 arrangement provides a comfortable ear engaging means in the form of the base of trough 38.

The FIG. 7 form of earpiece 16 corresponds to the FIG. 4 embodiment of the visor and includes a band 42 of a foam rubber or other spongy material to provide a fluid-tight seal and also a comfortable fit of the earpiece to the back of the user's ear. In this FIG. 7 form, the trough 8 itself is not extended behind the user's ear, but is preferably extended across the top of the ear whereupon it will flow down the scalp behind the ear with the ear itself being protected by the sealing band 42.

The FIG. 8 embodiment of earpiece 16 corresponds to the FIG. 5 cross-section of the brim portion of the visor. In this embodiment, the sealing means comprises a fluid-filled envelope 44 which is preferably merely an extension of the envelope 28 of FIG. 5. This envelope 44 provides a comfortable contact with the back of the user's ear while providing a fluid-tight seal to protect the user's ear. As with the FIG. 7 embodiment, the trough 8 is preferably extended across the top of earpiece 16 to direct the flow of fluid onto the user's scalp to flow down behind the ear with the ear being protected by the seal 44.

While the present invention has been illustrated in terms of particular apparatus, it is apparent that various modifications may be made within the scope of the present invention as defined by the appended claims:

I claim:

1. A visor for protecting a person's face and ears from a hairdressing material applied to the person's hair comprising:
   fluid sealing means for forming a fluid-tight seal against the person's skin extending across the person's forehead from one ear to the other, across the tops of both ears and down the back of both ears;
   a trough connected on a first edge to said sealing means and extending across the person's forehead from one ear to the other and extending further across the tops of both ears for directing fluids collected by said trough to points behind said ears;
   a brim extending from a second edge of said trough along that portion of said trough which extends across the person's forehead; and
   a pair of cup shaped earpieces connected to ends of said trough for holding said visor against the person's forehead in sealing fashion and for protecting the person's ears;
   said earpieces having upper edges extending from the second edge of those portions of said trough extending across the tops of said ears, rear edges connected to those portions of said sealing means extending down the back of said ears, and forward edges extending down the front of the person's ears in contact with the person's face.

2. Apparatus according to claim 1 wherein said visor is molded from a relatively soft plastic and said fluid sealing means comprises an extension of the first edge of said trough having a thin border positioned at an acute angle with respect to the person's forehead.

3. Apparatus according to claim 1 wherein said fluid sealing means is a band of resilient porous material bonded to said first edge of said trough.

4. Apparatus according to claim 1 wherein said sealing means comprises a fluid filled tubular member bonded to said first edge of said trough.

5. Apparatus according to claim 4 wherein said fluid is a liquid.

* * * * *